United States Patent [19]

Stock

[11] 4,149,004

[45] Apr. 10, 1979

[54] METHOD OF INHIBITING CUPRENE FORMATION IN ETHYNYLATION REACTION

[75] Inventor: Albert M. Stock, LaPorte, Tex.

[73] Assignee: E. I. Du Pont de Nemours and Company, Wilmington, Del.

[21] Appl. No.: 929,801

[22] Filed: Jul. 31, 1978

Related U.S. Application Data

[63] Continuation-in-part of Ser. No. 814,433, Jul. 11, 1977, abandoned.

[51] Int. Cl.$^2$ .............................................. C07C 29/00
[52] U.S. Cl. .................................................... 568/855
[58] Field of Search .......................................... 568/855

[56] References Cited

U.S. PATENT DOCUMENTS

| | | | |
|---|---|---|---|
| 3,560,576 | 2/1971 | Kirchner | 568/855 |
| 4,002,694 | 1/1977 | Hort | 568/855 |
| 4,093,668 | 6/1978 | Reiss et al. | 568/855 |

FOREIGN PATENT DOCUMENTS 1455761  11/1976  United Kingdom .................... 568/855

*Primary Examiner*—Joseph E. Evans

[57] ABSTRACT

When acetylene flow to the continuous, aqueous ethynylation reaction of formaldehyde and acetylene, using a copper acetylide complex as the catalyst, is interrupted, resulting cuprene formation can be inhibited by maintaining the reaction mass at a pH of 3.5–5 until normal acetylene flow is resumed.

5 Claims, No Drawings

METHOD OF INHIBITING CUPRENE FORMATION IN ETHYNYLATION REACTION

CROSS REFERENCE TO RELATED APPLICATION

This application is a continuation-in-part of application Ser. No. 814,433, filed July 11, 1977, now abandoned.

BACKGROUND AND SUMMARY OF THE INVENTION

The process of producing 1,4-butynediol by the continuous aqueous reaction of formaldehyde and acetylene using a copper acetylide complex as a catalyst (commonly called ethynylation), is well known. Such a process is shown, for example, in Kirchner, U.S. Pat. No. 3,650,985. The same process, using a bismuth-modified copper acetylide complex as the catalyst, is shown in U.S. application Ser. No. 794,674, filed May 6, 1977. The U.S. patent and the U.S. application are incorporated into this specification to show these processes.

When the flow of acetylene to such a reaction is interrupted because it is in short supply or because of an accident, and ethynylation stops momentarily, a significant amount of the copper acetylide catalyst is reduced to metallic copper. This metallic copper promotes the formation of cuprene, which clogs filters used in the process and reduces the catalyst's effectiveness.

It has now been found that this cuprene formation can be inhibited and the useful life of the catalyst extended if, when acetylene flow is interrupted, the pH of the reaction mass is reduced from the normal value of 6-8 to a value of about 3.5-5, and is held there until the normal flow of acetylene is resumed.

DETAILED DESCRIPTION OF THE INVENTION

When the flow of acetylene to such an ethynylation reaction is interrupted, the pH value of the reaction mass should be brought to about 3.5-5, preferably 3.5-4.0, as quickly as possible. When a bismuth-modified copper acetylide complex is used as the catalyst, the pH need be brought only to 4.5-5.

During the ethynylation reaction a basic material is normally added to the reaction mass, which keeps its pH value at about 6-8, preferably 6-7. Customarily used basic materials are sodium bicarbonate, sodium carbonate, sodium hydroxide and calcium carbonate. When the basic material used is soluble in the reaction mass, as is the case with sodium bicarbonate, sodium carbonate and sodium hydroxide, the pH can be brought into the range of 3.5-5 simply by slowing or stopping the flow of the basic material into the reaction mass. When the basic material used has limited solubility in the reaction mass and is therefore present in substantial excess, as is the case with calcium carbonate, the pH of the reaction mass is preferably brought into the range of 3.5-5 by the direct addition of acid. Any monocarboxylic acid can be used, provided it has an ionization constant of about $1 \times 10^{-3}$ to $1 \times 10^{-5}$, is miscible with water in all proportions and does not complex with the catalyst to form compounds which interfere with the ethynylation reaction. Illustrative of such acids are formic, acetic, propionic, acrylic and chloroacetic. Formic acid is preferred because it does not introduce a new class of compounds into the system.

The temperature of the reaction mass need be kept at no particular level during the period of acetylene flow interruption. It is desirable to keep the reaction mass at or near the reaction temperature so that little or no heating will be required when normal acetylene flow resumes, but the only real requirement is that the mass be kept from solidifying so that it can be agitated to keep the catalyst suspended.

During the period of acetylene flow interruption it is also desirable to keep the reaction mass under a nitrogen atmosphere to exclude oxygen and thus prevent formation of an explosive mixture when acetylene flow is resumed.

When acetylene flow resumes and the noncondensable portion of the atmosphere above the reaction mass contains at least 40% by volume of acetylene, the pH value of the reaction mass is quickly brought back to working level of 6-8, preferably 6-7, by the rapid addition of basic material, and ethynylation continues.

In the following examples all parts are by weight unless otherwise indicated.

EXAMPLES

Example 1

1,4-Butynediol was prepared by the continuous reaction of acetylene and formaldehyde, using a bismuth-modified copper acetylide complex as the catalyst, as shown in U.S. application Ser. No. 794,674, filed May 6, 1977. Saturated aqueous sodium bicarbonate solution was constantly fed into the reaction mass to keep its pH value in the range of 6-7.

During the reaction, the flow of acetylene to the reaction mass was accidentally interrupted. The pH of the reaction mass was brought to about 4.5 by immediately stopping the addition of sodium bicarbonate solution, and was held at that value until acetylene flow returned to normal, a matter of about 30 minutes. During this interval, the mass was kept under nitrogen.

After normal acetylene flow was restored, and the level of acetylene in the noncondensable portion of the reactor atmosphere reached 40% by volume, the pH of the reaction mass was brought back into the range 6-7 by resuming the addition of sodium bicarbonate solution.

At the end of 11 days, a sample of catalyst was taken. An X-ray diffraction scan showed only a trace of copper to be present.

Example 2

A 1-liter reactor was charged with 17 g of an ethynylation catalyst of the type described in U.S. Pat. No. 3,650,985, 6 g of calcium carbonate and 360 g of an aqueous 26.3% solution of formaldehyde.

The reaction mass and reactor vapor space were purged with acetylene and the reactor head acetylene pressure adjusted to give a partial pressure of 0.5 atmosphere over the reaction mass at 95° C. The reaction mass was continuously stirred and acetylene at this pressure was then continuously passed through the reaction mass and vented from the reactor while the temperature was raised to 95° C. over a period of 15 minutes. After 65 minutes of this at 95° C. and a pH of 6.0-6.2, the acetylene flow was stopped, the reactor depressurized and purged with nitrogen. The pH of the reaction mass was then reduced to 3.7 by the addition of 9 ml of 90% aqueous formic acid.

The mass was held for 75 minutes, under nitrogen, at 91°-96° C. The reactor was again purged with acetylene and 6 g of calcium carbonate were added to the reaction mass. The reactor was then pressurized with acetylene as before and operated normally at 95° C. and a pH of 6.1-6.3 for another 45 minutes.

At the end of the reaction, the catalyst was recovered. An X-ray diffraction scan of the catalyst gave no indication of the presence of metallic copper.

I claim:

1. In the continuous aqueous reaction of formaldehyde and acetylene to form 1,4-butynediol, run at a pH of 6-8 and using a copper acetylide complex as the catalyst, a method of inhibiting cuprene formation when the acetylene flow to the reaction mass is interrupted, the method comprising maintaining the reaction mass at a pH of about 3.5-5 until the normal flow of acetylene is resumed.

2. The method of claim 1 in which the pH is brought into the range 3.5-5 by adding to the reaction mass a monocarboxylic acid which has an ionization constant of about $1 \times 10^{-3}$ to $1 \times 10^{-5}$, is miscible with water in all proportions and does not complex with the catalyst or form a compound which interferes with the reaction.

3. The method of claim 2 in which the acid is formic acid.

4. The method of claim 1 in which the catalyst is modified with bismuth and the pH is maintained in the range of 4.5-5.

5. In the continuous aqueous reaction of formaldehyde and acetylene to form 1,4-butynediol, using a copper acetylide complex as the catlyst and the addition of a basic material to control pH in the range of 6-8, a method of inhibiting cuprene formation when the acetylene flow to the reaction mass is interrupted which comprises maintaining the formaldehyde-acetylene reaction mass at a pH of 3.5-5 by adjusting the rate of addition of basic material, until normal acetylene flow is resumed.

* * * * *